United States Patent [19]
Beck et al.

[11] Patent Number: 5,834,617
[45] Date of Patent: Nov. 10, 1998

[54] SELECTIVE DIMERIZATION OF PENTENENITRILE

[75] Inventors: William Allen Beck, Middletown; Frank Edward Herkes; David Page Higley, both of Wilmington, all of Del.

[73] Assignee: E. I. du Pont de Nemours and Company, Wilmington, Del.

[21] Appl. No.: 993,970

[22] Filed: Dec. 18, 1997

[51] Int. Cl.$^6$ .................................................. C07C 255/00
[52] U.S. Cl. ........................... 558/361; 558/377; 558/457
[58] Field of Search ..................................... 558/361, 377, 558/457

[56] References Cited

U.S. PATENT DOCUMENTS

| 4,211,725 | 7/1980 | Kluger et al. | 260/583 P |
| 4,260,556 | 4/1981 | Kluger et al. | 260/465.5 R |
| 4,941,954 | 7/1990 | Becker | 204/59 R |

*Primary Examiner*—Johann Richter
*Assistant Examiner*—Joseph Murray

[57] ABSTRACT

The present invention relates to a process for selective dimerization of 2-pentenenitrile or mixtures of 2- and 3-pentenenitrile in the presence of a strong base to form 1,3-dicyano-2-ethyl-3-hexene.

6 Claims, No Drawings

SELECTIVE DIMERIZATION OF PENTENENITRILE

The present invention relates to a process for selective dimerization of 2-pentenenitrile or mixtures of 2- and 3-pentenenitrile in the presence of a strong base to form 1,3-dicyano-2-ethyl-3-hexene. 1,3-Dicyano-2-ethyl-3-hexene may be converted into useful diamine or diacid derivatives.

BACKGROUND OF THE INVENTION

U.S. Pat. No. 4,941,954 taught the electrolytic coupling of unsaturated dinitriles in the presence of an electron conducting compound.

U.S. Pat. Nos. 4,211,725 and 4,260,556 taught the formation of a reaction product mixture of monocyanoamines, dicyanoamines and a mixture of dimers by the reaction of 2-pentenenitrile with ammonia or amines (nucleophilic agent). But none of these patents taught the selective formation of 1,3-dicyano-2-ethyl-3-hexene, a dimer of 2-pentenenitrile, from 2-pentene-nitrile or from mixtures of 2-pentenenitrile and 3-pentenenitrile. 1,3-Dicyano-2-ethyl-3-hexene may be hydrogenated to form a diamine or converted into a saturated or unsaturated diacid. The diamine product is a potential monomer for the formation of polyamides or polyurethaneureas or may be used as an epoxy curing agent. The diacid products may act as monomers for polymerization, and the unsaturated diacids may be reacted with nucleophiles in Michael type addition reactions to yield monomers having pendant groups linked to the molecular backbone by carbon, sulfur, phosphorous or nitrogen atoms.

SUMMARY OF THE INVENTION

The present invention is a process for selectively making 1,3-dicyano-2-ethyl-3-hexene by dimerizing 2-pentenenitrile or mixtures of 2- and 3-pentenenitrile comprising the steps of forming a reaction mixture containing 2-pentenenitrile or 2- and 3- pentenenitrile and a catalytic amount of strong organic base or inorganic base with or without the addition of a phase transfer agent to the reaction mixture, or optionally forming the reaction mixture in the presence of an inert solvent, water, or an inert solvent mixed with water wherein the organic base is incapable of undergoing a non-reversible addition reaction with the pentenenitrile; and reacting the mixture at a temperature of from about 0° to 160° C.

The base for the process is selected from the group consisting of NaOH, KOH, slaked lime, KF, KCN, organic bases formed from the reaction of an active metal with an alcohol, benzyltrimethylammonium hydroxide, alkali metal carbonates, alkaline earth oxides, alkaline earth carbonates, and tertiary amines.

If the base is formed from the reaction of an active metal with an alcohol, the compounds sodium methylate and potassium t-butylate are preferred.

Preferred inert solvent are selected from the group consisting of alcohols, tetrahydrofuran, dioxane, hexane and methyl-t-butylether. Such an inert solvent may be used alone or in combination with water. Water alone is also acceptable for use in the reaction mixture.

DETAILED DESCRIPTION

The present invention is a process for selectively making 1,3-dicyano-2-ethyl-3-hexene by dimerizing 2-pentenenitrile or mixtures of 2- and 3-pentenenitrile comprising the steps of forming a reaction mixture containing 2-pentenenitrile or 2- and 3-pentenenitrile and a catalytic amount of strong organic base or inorganic base with or without the addition of a phase transfer agent to the reaction mixture, or optionally forming the reaction mixture in the presence of an inert solvent, water, or an inert solvent mixed with water, wherein the organic base is incapable of undergoing a non-reversible addition reaction with the pentenenitrile; and reacting the mixture at a temperature of from about 0° to 160° C. If it is desired to run the present process at atmospheric pressure, a temperature range of from 0° to 75° C. is preferred. If it is desired to run the present process at temperatures in excess of 75° C., it is recommended that the process be run at a pressure which is greater than atmospheric. For example, at a temperature of 130° C., a pressure of about 500 psig is recommended. The reaction vessel may be pressurized using any inert gas, for example, nitrogen or argon.

The present process may be run as a batch or a continuous process.

The present process selectively dimerizes 2-pentenenitrile or mixtures of 2- and 3-pentene-nitrile to form the cis (E-I) and trans (Z-I) isomers of 1,3-dicyano-2-ethyl-3-hexene as shown below:

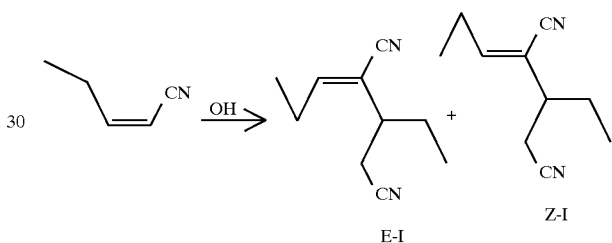

The pentenenitrile reactant may be either the cis or trans isomer and may be either the pure compound or compounds, mixtures of the cis and trans isomers of the pure compound or compounds or mixtures of crude compounds containing other organic materials such as other pentenenitriles, cyclohexane or benzene.

The strong base suitable for use in the present process may be a hydroxylic or a Lewis base and include strong hydroxylic bases such as NaOH, KOH, slaked lime, sodium methylate, potassium t-butylate and other reaction products of active metals (Na, K, Mg) with alcohols; benzyltrimethylammonium hydroxide, tertiary amines, alkali metal oxides and carbonates and alkaline earth metal oxides and carbonates or Lewis bases such as KF or KCN. The base may be used in the reaction mixture as the compound itself or a mixture of such basic compounds or the base may be supported on a solid substrate. Such solid substrates include metal oxides such as $Al_2O_3$, $ZrO_2$ or $TiO_2$, but may be any solid material that may carry a sufficient amount of the catalytic base and be suitable for use in the reaction. The base, itself, may be added as a solution or as a solid. The base may also have limited solubility in the reaction mixture or be insoluble in the reaction mixture.

If it is desired to use an organic base as a catalyst in the present process, it is essential that the base be incapable of undergoing a non-reversible addition reaction with the pentenenitriles. Bases such as ammonia, primary and secondary amines which undergo addition reactions with 2- or 3-pentenenitrile are not suitable for use in the present process since the addition reaction predominates and dimerization will neither occur selectively nor at any practicable yield. The presence of such reactive organic bases must be avoided in the present process. Noting this precaution, it may be possible to use certain hindered secondary amines as the catalytic base in the present process if the rate of dimerization catalyzed by the hindered secondary amine exceeds that of the non-reversible addition of the hindered secondary amine to the pentenenitriles.

When the base used in the reaction of the present process is an alkali metal or alkaline earth metal hydroxide, it is recommended to avoid exothermic polymerization that an inert solvent be used in the reaction mixture. Reaction rate and therefore the exotherm may also be controlled by controlling the concentration of the base, by using a base supported on a metal oxides such as such as $Al_2O_3$, $ZrO_2$ or $TiO_2$ or using bases having limited solubility in the reaction mixture.

In some cases to increase the rate of the dimerization reaction, it is helpful to add a phase transfer catalyst. Such catalysts include octyltrimethylammonium bromide (C8H17 (CH3)3NBr), tricaprylmethylammonium bromide, sodium dodecylsulfate and 18-crown-6 cyclic polyether. The phase transfer agent may be added to a reaction mixture formed from mixing the pentenenitriles with the strong base or may be added to a reaction mixture formed from mixing the pentenenitriles with the strong base and also including in the reaction mixture an inert solvent, water, or an inert solvent mixed with water.

An inert solvent may be present in the reaction mixture of the present process. The term inert means that the solvent will not interfere with the dimerization reaction or react with the pentenenitrile to produce unwanted by-products. Suitable solvents to use as diluents for the present process are solvents such as tetrahydrofuran, dioxane, hexane and methyl-t-butylether (MTBE). Water and alcohols may also be present in the reaction mixture. Both water and alcohols serve as proton sources. Other proton sources may also be present in the reaction mixture so long as they are not of sufficient acid strength to interfere with the action of the catalytic base.

The reaction of the present process is carried out at temperatures from about 0° to 160° and at pressures from atmospheric to 800 psig. The preferred reaction conditions are temperatures of from 0° to 75° C. and atmospheric pressure.

The products of the present invention are the E-I and the Z-I isomers of 1,3-dicyano-2-ethyl-3-hexene along with minor amount of trimer and higher oligomers. The relative amounts of the E-I to Z-I isomers as well as the selectivity of the process to the dimer vs. higher oligomers may be controlled by the selection of the catalytic base, the concentration of the catalytic base, selection of the reaction temperature and control of the other reaction variables. Selectivity of the dimerization by the present process is, in part, a function of the conversion of reactant pentenenitriles of the present process. At conversions of about 90%, the dimer selectivity is from about 40 to 70%. Selectivity of the relative amounts of E and Z isomers is related to the conversions of 2-pentenenitrile, and it was observed that the ratio of Z/E generally increases with increasing conversion of the pentenenitrile.

The following examples illustrate the present process, but are not intended to be limiting.

EXAMPLES

Example 1

1,3-Dicyano-2-Ethyl-3-Hexene from cis-2-Pentenenitrile and KOH in Methyl-t-Butylether A mixture of 600 ml methyl-t-butylether, 5 grams of powdered KOH, 0.5 gram tricaprylmethylammonium bromide and 200 ml cis-2-pentenenitrile was heated in a water bath and stirred magnetically at 45°–50° C. for two hours. After cooling to room temperature, 500 ml of water was added and the mixture shaken in a separatory funnel. The aqueous layer was extracted with additional methyl-t-butylether and the extract combined with the organic portion followed by drying over $MgSO_4$. The drying agent was removed by filtration and the solvent removed on a rotary evaporator. Gas chromatographic analysis of the residue indicated a 65% yield of 1,3-dicyano-2-ethyl-3-hexene isomers with a Z/E ratio of 6.1 at a 99% conversion of cis-2-pentene-nitrile. Distillation of the product on a 6 in. Vigreux column yielded a heart cut of 1,3-dicyano-2-ethyl-3-hexene in 98% purity having a boiling point of 90°–120° C. at 1 mm Hg. Subsequent distillations were performed on a 7 plate Oldershaw column.

Example 2

1,3-Dicyano-2-Ethyl-3-Hexene from cis-2-Pentenenitrile and Strong Bases in THF

To a stirred and heated mixture of 0.6 gram strong base in 25 ml THF at 25° was added 20 g (0.247 mole) cis-2-pentenenitrile over a 14 minute period. The temperature rose to 40° and was maintained there for a given length of time. GC analysis of the product showed the following results with different strong base catalysts.

| Base | Time Hr | % 2PN Conv. | % Dimer yld | Z/E ratio |
|---|---|---|---|---|
| KOH | 1 | 99 | 57.6 | 4.2 |
| NaOH | 4 | 96 | 45.6 | 3.0 |
| BzMe$_3$NOH | 1 | 99 | 41.4 | 5.6 |

Example 3

1,3-Dicyano-2-Ethyl-3-Hexene from Crude 2-Pentenenitrile and Aqueous NaOH Containing Octyltrimethylammonium Bromide Crude 2-pentenenitrile was substituted for high purity cis-2-pentenenitrile to demonstrate the selective dimerization amongst other isomeric pentenenitriles. The composition of the crude 2-pentenenitrile was:

| Component | wt % |
|---|---|
| cis-2-pentenenitrile | 73.0 |
| cis-2-methyl-2-butenenitrile | 11.7 |
| 2-methyl-3-butenenitrile | 3.8 |
| cyclohexane | 2.9 |
| benzene | 4.8 |
| trans-2-methyl-2-butenenitrile | 1.8 |
| trans-3-pentenenitrile | 2.8 |
| trans-2-pentenenitrile | 0.3 |

A mixture of 215.3 g crude 2-pentenenitrile, 26.9 grams NaOH, 107.7 grams water and 3.5 grams n-octyltrimethylammonium bromide was stirred vigorously in a oil jacketed round bottom flask at 50° for 6 hours. Analysis of the top organic layer showed a 82.7% conversion of cis-2-pentenenitrile and 58.4% yield of 1,3-dicyano-2-ethyl-3-hexene. No dimers were produced from the other pentene and butenenitriles.

Example 4

Solid Base Catalyzed Dimerization of cis-2-Pentenenitrile to 1-3,Dicyano-2-Ethyl-3-Hexene cis-2-Pentenenitrile (5.0 ml, 98.5%) was charged to a 20 ml cylindrical glass bottle containing 0.2–0.4 g solid catalyst. The glass tube was inserted into a jacketed stainless steel tube, containing a port for gas addition, and sealed. The tube was heated and shaken at 160° C. for 3 hours under 200 psig nitrogen pressure. Upon completion, the tube was cooled, depressured and product filtered from the catalyst. Analysis of the liquid product was performed on a 30 m×0.5 mm DB1701 megabore capillary column. A summary of catalysts and yield are found in Table I below:

Solid Base Catalyzed Dimerization of 2PN

| Catalyst | wt.cat. g | 2PN Conv. % | I Sel % | Z/E |
|---|---|---|---|---|
| KOH/Al2O3* | 0.2 | 80 | 59.5 | 2.0 |
| KOH/Al2O3 | 0.4 | 98 | 58.2 | 4.0 |

*this run was made at 130° C. The other data in this table were collected at 160° C.

What is claimed is:

1. A process for selectively making 1,3-dicyano-2-ethyl-3-hexene by dimerizing 2-pentenenitrile or mixtures of 2- and 3-pentenenitrile comprising the steps of forming a reaction mixture containing 2-pentenenitrile or 2- and 3-pentenenitrile and a catalytic amount of strong organic base or inorganic base with or without the addition of a phase transfer agent to the reaction mixture, or optionally forming the reaction mixture in the presence of an inert solvent, water, or an inert solvent mixed with water, wherein the organic base is incapable of undergoing a non-reversible addition reaction with the pentenenitrile; and reacting the mixture at a temperature of from about 0° to 160° C.

2. The process of claim 1 wherein the base is selected from the group consisting of NaOH, KOH, slaked lime, KF, KCN, organic bases formed from the reaction of an active metal with an alcohol, benzyltrimethylammonium hydroxide, alkali metal carbonates, alkaline earth oxides, alkaline earth carbonates, and tertiary amines.

3. The process of claim 2 wherein the base formed from the reaction of an active metal with an alcohols is sodium methoxide or potassium t-butoxide.

4. The process of claim 1 wherein the inert solvent is selected from the group consisting of alcohols, tetrahydrofuran, dioxane, hexane and methyl-t-butylether.

5. The process of claim 1 wherein the base is supported on a metal oxide or other solid substrate.

6. The process of claim 5 wherein the metal oxide is selected from the group consisting of $Al_2O_3$, $ZrO_2$ and $TiO_2$.

* * * * *

UNITED STATES PATENT AND TRADEMARK OFFICE
CERTIFICATE OF CORRECTION

PATENT NO. : 5,834,617
DATED : November 10, 1998
INVENTOR(S) : William Allen Beck, et. al.

It is certified that error appears in the above-identified patent and that said Letters Patent is hereby corrected as shown below:

Title page, item[75], inventors: should read --David Page Higley --.

Signed and Sealed this

Twelfth Day of January, 1999

Attest:

Attesting Officer

Acting Commissioner of Patents and Trademarks